United States Patent [19]

Breivik et al.

[11] Patent Number: 5,502,077

[45] Date of Patent: Mar. 26, 1996

[54] FATTY ACID COMPOSITION

[75] Inventors: Harald Breivik, Skjelsvik; Bernt Borretzen, Porsgrunn; Knut H. Dahl, Ulefoss; Hans E. Krokan, Sjetnemarka; Kaare H. Bonaa, Tromso, all of Norway

[73] Assignee: Norsk Hydro A.S., Oslo, Norway

[21] Appl. No.: 902,500

[22] Filed: Jun. 23, 1992

Related U.S. Application Data

[63] Continuation of Ser. No. 389,902, Aug. 4, 1989, abandoned.

[30] Foreign Application Priority Data

Aug. 11, 1988 [GB] United Kingdom ............... 8819110

[51] Int. Cl.$^6$ .......................... A61K 31/23; A61K 31/19
[52] U.S. Cl. .......................... 514/560; 514/549; 514/578
[58] Field of Search .................... 514/549, 578, 514/560; 554/8, 18

[56] References Cited

U.S. PATENT DOCUMENTS

| | | | |
|---|---|---|---|
| 3,158,541 | 11/1964 | Sutherland | 514/549 |
| 4,415,554 | 11/1983 | Horribin et al. | 514/549 |
| 4,526,902 | 7/1985 | Rubin | 424/312 |
| 4,564,475 | 7/1986 | Masalchiro | 514/549 |
| 4,615,839 | 10/1986 | Seto et al. | 260/412 |
| 4,675,132 | 6/1987 | Stout et al. | 260/421 |
| 4,681,896 | 7/1987 | Horribin et al. | 514/549 |
| 4,758,592 | 7/1988 | Horribin et al. | 514/549 |
| 5,130,061 | 7/1992 | Cornieri et al. | 554/167 |

FOREIGN PATENT DOCUMENTS

| | | |
|---|---|---|
| 0175468 | 3/1986 | European Pat. Off. . |
| 0283140A3 | 9/1988 | European Pat. Off. ............ 514/549 |
| 0292846 | 11/1988 | European Pat. Off. . |
| 63-088159 | 4/1988 | Japan . |
| 2033745 | 5/1980 | United Kingdom . |
| 1604554 | 12/1981 | United Kingdom . |
| 2090529 | 7/1982 | United Kingdom . |
| 2148713 | 6/1985 | United Kingdom . |
| 2197199 | 5/1988 | United Kingdom . |
| WO87/02247 | 4/1987 | WIPO . |
| WO88008444 | 11/1988 | WIPO . |
| WO89/11521 | 11/1989 | WIPO ................................ 260/412 |

OTHER PUBLICATIONS

Luly, Nutrition Lances, 1990, pp. 123 to 125.
Bonaa, et al New England J. of Medicine 322: 795–801, 1990.
Blonk, Am J. Clin Nutl. 1990:52 120–7.
Reis, et al Am. J. Cardiology 1990: 66 1171–1175.
Kinsella et al. Seafoods and Fish Oils in Human Health and Disease (New York, Marcel Dekka Inc. 1987) pp. 7+08.
Merck Index, 11th Ed. (Rahway, NJ. Merck and Co., 1989) p. 5784.
Treatment of Hypolipidemia, National Board of Health and Welfare Drug Information Center, Sweden, 1989 pp. 131 and 147 to 158.
Bernardi et al., Acta Toxicol. Ther., vol. 8 (3) pp. 339–352, published Mar. 1987.

*Primary Examiner*—Mukund J.g232 2 Shah
*Assistant Examiner*—P. K. Sripada
*Attorney, Agent, or Firm*—Fitzpatrick, Cella, Harper & Scinto

[57] ABSTRACT

Fatty acid composition comprising at least 80% by weight of omega-3-fatty acids, salts or derivatives thereof, wherein (all-Z)-5,8,11,14,17-eicosapentaenoic acid (EPA) and (all-Z)-4,7,10,13,16,19-docosahexaenoic acid comprises at least 75% by weight of the total fatty acids. The compositions can be used for the treatment or prophylaxis of multiple risk factors for cardiovascular diseases.

12 Claims, No Drawings

FATTY ACID COMPOSITION

This application is a continuation of application Ser. No. 07/389,902 filed Aug. 4, 1989, now abandoned.

Present invention relates to a fatty acid composition comprising at least 80% by weight of omega-3 polyunsaturated fatty acids, wherein at least 75% by weight of the total fatty acids comprise omega-3 (all-Z)-5,8,11,14,17-eicosapentaenoic acid (EPA) C 20:5 and (all-Z)-4,7,10,13,16,19-docosahexaenoic acid (DHA) C 22:6.

FIELD OF INVENTION

Cardiovascular diseases leading to morbidity and premature mortality is related to several risk factors such as hypertension, hypertriglyceridemia, hypercholesterolemia, high blood platelet aggregation and according to recent findings, a high activity of the blood coagulation factor VII phospholipid complex. Over the last three decades antihypertensive drugs have contributed to the decline in cardiovascular disease-related morbidity and mortality. There is however heightened concern about side effects and toxicity associated with the current antihypertensive therapy, especially in the mild hypertensive patient. There are results indicating that although the presently used antihypertensive agents are efficient in reducing blood pressure the pulse rate is coincidentally enlarged. Thus there is a need for a drug with fewer adverse effects for the treatment of hypertension. It would be particularly advantageous if such a drug could be used for the simultaneous treatment of all the above mentioned multiple risk factors associated with cardiovascular diseases, which is generally not the case with the currently available antihypertensive drugs.

DESCRIPTION OF PRIOR ART

During the last decade numerous publications have appeared which report that various dietary fish oil preparations containing omega-3 polyunsaturated fatty acids have an effect on serum cholesterol and blood platelet aggregation. The mechanisms suggested for these effects often center around the prostanoid system. Thus there is some information on how dietary fish oils alter the excretion of some prostaglandin metabolites but available data conflict on several points.

A reduction of blood pressure has been reported after intake of fish, crude fish oil (starting at 7% EPA and 5% DHA) or slightly concentrated fish oil preparations (typically containing 18% EPA and 12% DHA) although the components responsible for these effects were never identified. Furthermore all the studies presented so far had one or more serious flaws as pointed out in reviews of the available studies [H. R. Knapp et al., Proceedings of AOCS Short Course on polyunsaturated Fatty Acids and Eicosanoids, Ed. W. E. M. Lands, pp.41–55, American Oil Chemists Society] and [K. Bønaa, Tidskr. Nor Lægeforen nr. 28,1987, 2425–8].

Eicosapentaenoic acid C 20:5 omega 3 (EPA) has been considered to be the most important of the marine omega-3 polyunsaturated fatty acids partly because of its potent antiaggregatory action i.a. reported in U.S. Pat. No. 4,097,602, and Silver et al, which was filed in August 1974. Later Dyerberg et al also described the same effect in [Lancet, p.152, Jan.21, 1978] and [Lancet II,p 117–119, Jul. 15, 1978]. The main reason for the assumed importance of EPA is probably that it belongs to the eicosanoids, which are key substances for the prostaglandin metabolism.

However, according to several recent reports, EPA alone does not have a significant effect on hypertension. In ["Effects of highly purified eicosapentaenoic acid to angiotensin II and norepinephrine in the rabbit", Prostaglandins August 1986 Vol. 32, No 2, pp 179–187] no reduction of blood pressure in rabbits was obtained using highly purified EPA of 90% concentration. [Terano et al, Atherosclerosis, 46, 321–331, (1983)] reported that a preparation containing 75% EPA and 6.2% DHA had no significant effect on blood pressure in healthy volunteers after an intake of 3.6 g EPA ethyl ester. Similarly, [Yoshida et al, Artery, 14, 295–303, 1987], reported no effect on basal blood pressure after intake of 900 mg EPA ethyl ester for 14 days or more. Furthermore 90% EPA methyl ester had no effect on spontaneously hypertensive rats. [K. Yin et al, 1988, Clinical and Experimental Pharmacology and Physiology 15, 275–280].

In contrast to this, British patent application 2197199 describes a composition for combatting pregnancy-induced hypertension where the compositions used in the example had an EPA content of 28–35%. The patients had no earlier history of hypertension. Hypertension being developed under pregnancy is considered to have different biological causes than normal hypertension, which seems to be underlined by the fact that it usually disappears after the termination of the pregnancy.

To our knowledge there is nothing to suggest that DHA alone has any effect on the blood pressure.

According to U.S. Pat. No. 3,082,228 based on an application filed Dec. 18, 1959 a product containing at least 60% polyunsaturated fatty acids having 20 C atoms or more lowers the blood cholesterol content significantly. Although other early studies indicate that fish oils lower total cholesterol and LDL-cholesterol and raises HDL-cholesterol, later results have generally drawn the opposite conclusion, as pointed out by W. S. Harris in [(n-3)news, 3 (4), 1–7]. Thus, when summarizing 45 articles on the subject, he found that LDL-cholesterol was increased by 2–30%, depending on the type of hyperlipidaemia.

From PCT/WO 87/02247 is known a lipid emulsion for parenteral use comprising an emulsifier, water and a marine oil comprising at least one omega-3 fatty acid wherein the concentration of the free fatty acid in the emulsion is below about 5 meq/l, and wherein the marine oil will contain at least 30% by weight of a combination of esters of EPA and DHA. This lipid emulsion is used for the intravenous treatment of thrombotic disease states.

SUMMARY OF THE INVENTION

It has now been found that fatty acid compositions containing a high concentration, of at least 80% by weight, of omega-3 fatty acids, salts or derivatives thereof, where EPA and DHA are present in relative amounts of 1:2 to 2:1, and constitute at least 75% of the total fatty acids, has a surprisingly advantageous effect on all the above mentioned risk factors for cardiovascular diseases, but especially a good effect on mild hypertension, hypertriglyceridemia and on the coagulation factor VII phospholipid complex activity. It lowers serum LDL-cholesterol, increases serum HDL-cholesterol, lowers serum triglycerides, lowers systolic and diastolic blood pressure and the pulse rate and lowers the activity of the blood coagulation factor VII-phospholipid complex. Although the detailed biological mechanisms for the effects of the compositions according to present application are not explicitly known, there are indications of a surprising synergism between the action of EPA and of DHA.

One advantage of the compositions according to the present application is their being very well tolerated, not giving rise to any severe side effects.

An especially preferred composition according to the present application comprises at least 90% by weight of long chain, polyunsaturated omega-3 fatty acids of which EPA and DHA constitute at least 85% by weight of the total fatty acids and are present in a ratio of EPA:DHA from 1:1 to 2:1, especially about 3:2.

In order to isolate EPA and DHA in a mixture of high concentration according to the present application, a special method was developed for purifying and isolating the long chain fatty acids from natural fish oils. Compositions according to present application may be produced according to the method of our European Patent Application No.86906964.1. The analysis in % by weight was based on the ethyl esters even if other derivatives or salts or the acids themselves are a part of the present invention.

DETAILED DESCRIPTION OF THE INVENTION

The composition according to this invention is preferably produced via the following method. Initially the marine oil raw material is esterified and concentrated via urea fractionation or the like, where the conditions are sufficiently mild to avoid disintegration of the products. The second stage is a molecular distillation.

The fractionation in principle initially removes the major part of the esters having chain length below C 20. Thereafter a main fraction is removed consisting essentially of esters of the C 20— and C 22 acids. As the urea fractionation removes the saturated and less unsaturated esters, this fraction will contain high concentrations of EPA and DHA, according to the present method at least 75% by weight. The total amount of the long chain omega-3 acids will be at least 80% by weight. Other preferred compositions according to present application contain at least 95% by weight, with the EPA plus DHA content being at least 90% by weight. Another preferred composition according to present application contains at least 85% by weight of the total omega-3 fatty acids and an EPA and DHA amount of at least 80% by weight.

Other omega-3 acids of the C 20, C 21 and C 22 series will be obtained approximately in their original concentrations, e.g. from 3–5% by weight, typically at least 4.5% by weight. Thus the special and odd-numbered omega-3 all-Z 6, 9, 12, 15, 19-heneicosapentaenoic acid C 21:5 is normally present in concentrations of at least 1.5% by weight and omega-3 all-Z 7,10,13,16,19-docosapentaenoic acid normally in concentrations of about 3.0% by weight.

After removing the urea precipitate, the solvent used, normally ethanol, is partially or fully removed by evaporation and the esters thus isolated may be further purified by washing with water or a slightly alkaline water solution if the pure esters without contamination of the acids should be isolated.

The free acids may be produced by well known hydrolyzation procedures.

The upgrading of the EPA fraction to obtain a weight ratio of EPA:DHA of from 1:1 to 2:1, especially 3:2 or the upgrading of the DHA fraction to obtain a EPA:DHA weight ratio of from 1:1 to 1:2 may be achieved in the molecular distillation stage. The method also provides the possibility of using supercritical fluid extraction and/or chromatography in the second stage with $CO_2$ eventually containing a more polar modifier, such as ethanol, in order to concentrate the EPA and/or DHA fraction.

The urea fractionation and the subsequent molecular distillation are performed under gentle conditions to avoid oxidation and/or isomerisation of the highly unstable omega-3 acids. As seen from Table 1 and 2 below, which gives the analysis of products obtained in accordance with the method of this invention, there was not more than 1% of unknown components in the purified product. There are, however, a certain amount of minor products such as C-16 and C-18 acids as will appear from the detailed analyzis shown in Table 2.

For the main part these products will be the combined sum of the fraction of fatty acid esters, which are naturally occurring in fish oils, but the concentration of each separate ester in the finished product is less than 0.2%, apart from the omega-3 octadecatetraenoic acid C 18:4 n-3, which is present in approximately the same amount as in the starting material.

Thus it will be understood that the total concentration of byproducts occurring from the process is very low.

The process is flexible enough to affect the relative proportions between the long chain C 20, C 21 and C 22 fatty acids which occur naturally in available fish oil raw materials. It provides not only for the upgrading of the individual acids, but the ratio between them will remain within a pattern of variation which is optimal in nature. But simultaneously there is room for compensating the sometimes extreme variations which may occur naturally, cfr. below. Thus it will be possible to make a product with a constant and predetermined composition.

Fish oils may also contain by-products and contaminants such as pesticides, chlorinated hydrocarbons, heavy metals, cholesterol and vitamins. During the production of the concentrate, the concentrations of these components are significantly reduced compared to untreated fish oils.

In nature the relative contents of EPA and DHA, and also of the other long chain omega-3 acids, is dependent on the marine species and there are also seasonal variations within the same species. In the USA fish oil is today mainly produced from menhaden. This oil will typically contain 14–19% EPA and 5–8% DHA. Our analysis of one cod liver oil batch showed a content of 6.9 EPA and 8.4 DHA. For capelin the EPA values varied from 8.6 to 11.4 from January 1973 to August 1973, while the DHA values from 6.7% to 11% during the same period. For Norwegian coastal herring the content in October 1973 was 6.4% EPA and 9.8% DHA, while catches in November 1983 showed a reduction to 1.7% and 1.1%, respectively.

These variations mean that dietary intake of fish oils or fish alone, will not secure a constant supply of omega-3 acids. Even if all the long chain C 20, C 21 and C 22 omega-3 acids will not or only may become moderately upgraded during the process, they will be preserved at least in their original proportions.

In Table 1 the left hand column illustrates the typical variations between the contents of individual long chain acids in the compositions of this invention, while the right hand column shows the exact analysis of the test sample used in the study on the biological effects, the results of which are shown in the Tables 4–8 below.

TABLE 1

| | Typical product variation | Test Sample |
|---|---|---|
| C 20:4 omega-6 | 1–2 | 1,4 |
| C 20:5 omega-3 | 40–60 wt % | 54 wt % |
| C 21:5 omega-3 | 1–4 wt % | 1,5 wt % |
| C 22:5 omega-3 | 1–3 wt % | 2 wt % |
| C 22:6 omega-3 | 25–45 wt % | 32,6 wt % |
| lower acids | 3–8,5 wt % | 7,5 wt % |
| unknown | 1 wt % | 1 wt % |
| sum Omega-3 FA | | 90.1 wt % |
| sum EPA + DHA | | 86.6 wt % |
| EPA : DHA | | 3.3:2 |

Table 2 shows a detailed analysis of a batch of starting material and of another composition of this invention obtained therefrom.

TABLE 2

| | Fatty acid composition (%) | |
|---|---|---|
| Fatty acid | Starting material Fish oil, | Product ethyl ester test sample |
| C14:0 | 7.6 | 0.0 |
| Pristanate | 0.4 | 0.0 |
| C16:0 | 19.1 | 0.0 |
| C16:1 n7 | 7.2 | 0.0 |
| 7-Me16:0 | 0.3 | 0.0 |
| C16:2 n6 | 0.5 | 0.0 |
| C16:2 n4 | 1.2 | 0.0 |
| Phytanate | 0.3 | 0.0 |
| C16:3 n4 | 0.5 | 0.0 |
| C16:4 n1 | 1.0 | 0.2 |
| C18:0 | 2.3 | 0.0 |
| C18:1 n9 | 9.1 | 0.0 |
| C18:1 n7 | 3.0 | 0.0 |
| C18:1 n5 | 0.4 | 0.1 |
| C18:2 n6 | 1.1 | 0.0 |
| C18:2 n4 | 0.2 | 0.0 |
| C18:3 n6 | 0.2 | 0.2 |
| C18:3 n3 | 0.7 | 0.2 |
| C18:4 n3 | 2.5 | 2.8 |
| C18:4 n1 | 0.1 | 0.2 |
| C20:1 n9 + 7 | 5.9 | 0.0 |
| C20:1 | 0.1 | 0.0 |
| C20:2 n6 | 0.2 | 0.1 |
| C20:3 n6 | 0.1 | 0.0 |
| C20:4 n6 | 0.7 | 1.4 |
| C20:4 n3 | 1.2 | 0.9 |
| C20:5 n3 | 16.5 | 53.4 |
| C22:1 n11 + 9 | 4.6 | 0.0 |
| C22:2 n6 | 0.7 | 0.0 |
| C21:5 n3 | 0.9 | 1.6 |
| C22:4 n6 | 0.1 | 0.0 |
| C22:5 n6 | 0.1 | 0.4 |
| C22:5 n3 | 2.0 | 3.1 |
| C22:6 n3 | 7.9 | 34.3 |
| Sum unknown | 1.0 | 1.0 |
| Sum omega-3 FA | 31.7 | 95.4 |
| incl. C 18 | 3.2 | 3.0 |
| Sum EPA + DHA | 24.4 | 87.7 |
| EPA:DHA | 2.1:1 | 3.1:2 |

Table 3 shows the main fatty acid contents of several compositions according to present application.

TABLE 3

| Fatty acid | Composition (%) | | | | | |
|---|---|---|---|---|---|---|
| C18:2 n6 | 0.3 | 0.3 | 0.1 | 0.0 | 0.2 | 0.1 |
| C18:3 n3 | 0.3 | 0.3 | 0.0 | 0.1 | 0.3 | 0.0 |
| C18:4 n3 | 2.3 | 2.3 | 3.6 | 2.2 | 1.8 | 0.7 |
| C18:4 n1 | 0.2 | 0.2 | 0.4 | 0.3 | 0.0 | 0.0 |
| C20:4 n6 | 1.7 | 1.7 | 1.5 | 3.9 | 1.6 | 1.6 |
| C20:4 n3 | 2.4 | 0.9 | 1.3 | 1.2 | 1.9 | 0.3 |
| C20:5 n3 | 54.7 | 52.7 | 42.2 | 48.5 | 41.0 | 31.7 |
| C21:5 n3 | 2.1 | 2.1 | 1.7 | 2.0 | 1.7 | 1.2 |
| C22:5 n6 | 0.4 | 0.4 | 0.6 | 0.8 | 0.7 | 1.1 |
| C22:5 n3 | 5.4 | 5.8 | 2.8 | 4.3 | 5.8 | 3.3 |
| C22:6 n3 | 28.7 | 31.0 | 38.0 | 34.9 | 42.4 | 58.5 |
| Sum n3FA incl. C 18 | 95.9 | 95.1 | 89.6 | 93.2 | 94.9 | 95.7 |
| Sum EPA + DHA | 83.4 | 83.7 | 80.2 | 83.4 | 83.4 | 90.2 |
| EPA:DRA | 1.9:1 | 1.7:1 | 1.1:1 | 1.4:1 | 1:1 | 1:1.8 | n3FA denotes omega-3 fatty acids

BIOLOGICAL EFFECTS

In order to evaluate the effect of a composition according to present application on blood pressure, pulse rate, triglyceride levels, serum cholesterol and HDL-cholesterol, blood platelet aggregation and the coagulation factor VII phospholipid complex activity, the whole population aged 34–60 years, of a small Norwegian town was invited to a health check and of those, 22000 persons were screened for the following criteria:

untreated moderate hypertension of a diastolic blood pressure (DBP) ranging from 89 to 111 mm Hg and a systolic blood pressure (SBP) from 110 to 180 mmHg.

no previous cardiac illness and not using cardiac drugs no severe diseases not extremely overweight no alcoholism serum cholesterol of at least 6.0 mmol/liter The group of volunteers selected by these criteria amounted to 172 persons. The volunteers were screened during a run-in period of 6 month to ensure stabilization of blood pressure before the test substance was administered.

All blood pressure measurements were done with an automatic instrument (Dinamap) and at each occasion three measurements (with 2 minutes intervals) were done sitting and standing under controlled conditions. The average of the two last sitting and standing measurements were used.

The study was a controlled double blind one. The 172 volunteers were randomized to two groups of similar size. One group was treated with placebo capsules of corn oil, each with 1 g corn oil added 0.3% Vitamin E. The other group received capsules containing 1 g of the test substance whose composition is given in Table 1. Both sets of capsules were made of coloured soft gelatin to assure the blind effect. The volunteers were asked to take 3 capsules twice daily of either the test or control substance for 11 to 12 weeks. 171 volunteers completed the study and on average about 90% of the capsules were taken.

As will appear from tables 4 and 5 below, corn oil had no statistically significant effect on the blood pressure. The effect on the test substance on blood pressure was assessed first on the whole group taking the test substance and next on those individuals with higher blood pressures. The average blood pressures for the patients with higher blood pressures at the start and finish of the treatment with the active test substance of this invention are given in Table 4 (diastolic blood pressure) and Table 5 (systolic blood pressure).

TABLE 4

EFFECT OF TEST SUBSTANCE AND CORN OIL ON DIASTOLIC BLOOD PRESSURE

| DBP Range | Number of patients | Average DBP before treatment (mm HG) | Average DBP after treatment (mm Hg) | Average Reduction in DBP (mm Hg) | Significance |
|---|---|---|---|---|---|
| Test substance | | | | | |
| 85–109 | 62 | 95.8 | 93.4 | 2.4 | $p < 0.05$ |
| 98–109 | 22 | 102 | 96.2 | 5.8 | $p < 0.01$ |
| Corn oil | | | | | |
| 85–109 | 57 | 95.7 | 96.0 | 0 | n.s. |
| 98–109 | 26 | 101.8 | 100.7 | 1.1 | n.s. | n.s. means not significant

TABLE 5

EFFECT OF TEST SUBSTANCE AND CORN OIL ON SYSTOLIC BLOOD PRESSURE

| SBP of patients (mm Hg) | Number of patients | Average SBP before treatment (mm HG) | Average SBP after treatment (mg Hg) | Average Reduction in SBP (mm Hg) | Significance |
|---|---|---|---|---|---|
| Test substance | | | | | |
| >135 | 71 | 148.1 | 144.5 | 3.6 | $p < 0.05$ |
| >150 | 24 | 158.4 | 150.3 | 8.1 | $p < 0.001$ |
| >155 | 15 | 162.2 | 152.4 | 9.8 | $p < 0.001$ |
| Corn oil | | | | | |
| >135 | 62 | 148.5 | 149.6 | 0 | n.s. |
| >150 | 23 | 159.1 | 158.0 | 1.1 | n.s. |
| >155 | 17 | 161.8 | 159.6 | 2.2 | n.s. |

As is evident from the above tables, the test substance had a highly significant hypotensive effect both on systolic and diastolic blood pressure. It is also clear that the effect is strongest on those patients with the highest blood pressure. No significant effect was obtained in the corn oil group.

TABLE 6

EFFECT OF TEST SUBSTANCE AND CORN OIL ON SYSTOLIC AND DIASTOLIC BLOOD PRESSURE ACCORDING TO DIETARY INTAKE OF FISH (DISHES PER WEEK)

| Dishes per week | Number of patients | | Average BP before treatment (mm HG) | Average BP after treatment (mm Hg) | Average Reduction in BP (mm Hg) | Significance |
|---|---|---|---|---|---|---|
| Test substance | | | | | | |
| 0–2 | 44 | SBP | 145.3 | 139.3 | −6.9 | $p = 0.005$ |
|  |  | DBP | 99.8 | 94.0 | −5.7 | $p = 0.0001$ |
| 3–5 | 34 | SBP | 143.6 | 141.2 | −2.4 | $p = 0.2$ |
|  |  | DBP | 97.7 | 96.3 | −1.4 | $p = 0.2$ |
| Corn oil | | | | | | |
| 0–2 | 34 | SBP | 145.2 | 146.8 | +1.6 | $p = 0.4$ |
|  |  | DBP | 98.3 | 100.2 | +1.9 | $p = 0.1$ |
| 3–5 | 44 | SBP | 142.3 | 143.4 | +1.1 | $p = 0.5$ |
|  |  | DBP | 97.4 | 97.9 | +0.5 | $p = 0.7$ |

As appears from Table 6 a good hypotensive effect is achieved with the composition according to present application, surprisingly so even in the group with a high dietary intake of fish of 3–5 dishes per week. In comparison, no beneficiary effect is achieved with corn oil.

The results shown above indicate that a composition according to present application gives a surprisingly much better effect than a dietary intake of fish or slightly concentrated marine oil would lead one to expect. This is probably due to a synergistic effect of EPA and DHA.

Compared with the test results achieved in the previously conducted studies with a dietary intake of marine fish oils, the results achieved with a composition according to the present application show a surprising improvement in effect on diastolic and systolic bloodpressure of a slightly hypertensive patient and a more hypertensive patient of, respectively, approximately 30% and 45%.

TABLE 7

EFFECT OF TEST SUBSTANCE AND CORN OIL ON PULSE RATE (per minute)

| Group | Before | After | Change | Significance |
|---|---|---|---|---|
| Test subst | | | | |
| sitting | 75.4 | 73.2 | −2.2 | $p < 0.02$ |
| standing | 82.9 | 80.2 | −2.7 | $p < 0.005$ |
| Corn Oil | | | | |
| sitting | 74.3 | 75.1 | +0.8 | $p = 0.3$ |
| standing | 80.9 | 82.2 | +1.3 | $p = 0.2$ |

The pulse rate study included 78 persons in the group recieving the test substance and 77 persons in the other group.

As will appear from the Table above there was obtained a significant lowering in pulse rate with the test substance according to present application and a slight not significant raise of pulse rate with corn oil.

TABLE 8

EFFECT OF TEST SUBSTANCE AND CORN OIL
ON SERUM CHOLESTEROL (mmol/liter)

| GROUP | BEFORE | | AFTER | |
|---|---|---|---|---|
| | Tot. chol. | HDL Chol. | Tot. Chol. | HDL Chol. |
| All Patients: | | | | |
| Test substance (n = 78) | 6.58 | 1.35 | 6.57 | 1.41** |
| Corn oil (n = 78) | 6.68 | 1.33 | 6.64 | 1.41** |
| Tot. Chol.>7 | | | | |
| Test substance (n = 26) | 7.74 | 1.53 | 7.31** | 1.58* |
| corn oil (n = 20) | 7.66 | 1.26 | 7.45* | 1.32* |

*$p < 0.1$
**$p < 0.01$

As appears from Table 8 the test composition according to present application lowers total serum cholesterol significantly in patients with a total cholesterol of above 7.0 mmol/liter and raises HDL cholestrol significantly in the whole population. Similar, but weaker effects are obtained in the corn oil group.

The compositions according to present application further lower LDL-cholesterol by 5–10% in patients with total cholesterol >7 mmol/l but has no significant effect in patients with a total cholesterol of <6.5 mmol/l.

TABLE 9

EFFECT OF TEST SUBSTANCE AND
CORN OIL ON SERUM TRIGLYCERIDE

| Group | n | Before | After | Reduction | p-value |
|---|---|---|---|---|---|
| | | Triglyceride (mmol/l) | | | |
| TEST SUBSTANCE | 87 | 1.51 | 1.20 | 0.31 | 0.001 |
| CORN OIL | 85 | 1.57 | 1.47 | 0.03 | NS |
| Patients with triglycerides > 2.00 mmol/l | | | | | |
| TEST SUBSTANCE | 14 | 3.28 | 2.03 | 1.25 | 0.0001 |
| CORN OIL | 17 | 3.22 | 2.66 | 0.56 | 0.01 |

As appears from Table 9, the test substance has the effect of lowering the level of serum triglycerides, especially in patients with high levels (>2.0 mmol/l) before treatment. No significant effect is obtained with corn oil in the whole group of volunteers, whereas a very small effect is obtained in persons with high levels of triglycerides.

TABLE 10

EFFECT OF TEST SUBSTANCE AND CORN OIL
ON BLOOD PLATELET AGGREGATION

| Group | n | Collagen 0,2 ug/ml | | Collagen 0,1 ug/ml | |
|---|---|---|---|---|---|
| | | Before $\bar{X}$ SEM | After $\bar{X}$ SEM | Before $\bar{X}$ SEM | After X SEM |
| TEST SUBST | 21 | 63.4 ± 4.40 | 38.8 ± 5.19 | 38.0 ± 5.91 | 13.7 ± 3,77 |
| CORN OIL | 21 | 73.5 ± 4.40 | 57.4 ± 6.37 | 43.4 ± 45.5 | 15.2 ± 3.32 |

As will appear from Table 10, the compositions according to present application have a blood platelet antiaggregating effect.

The coagulation factor VII-phospholipid complex is found in the plasma from men belonging to a high risk group for cardiovascular diseases, as described in [P. Leren et al, The Oslo Study, Cardiovascular disease in middle aged and young Oslo men. *Acta Med. Scand,* suppl.588,1–38, (1987)] and [Dalaker et al, A novel form of factor VII in plasma from men at risk for cardiovascular disease, *Br.J. Haematol.,* 61, 315–322, (1985)], and is considered to be another risk factor for cardiovascular disease.

TABLE 11

EFFECT OF TEST SUBSTANCE AND CORN OIL
ON COAGULATION FACTOR VII PHOSPHOLIPID
COMPLEX ACTIVITY (PER CENT)

| Group | n | Before | After | Difference |
|---|---|---|---|---|
| TEST SUBST | 69 | 9.7 | 6.6 | 3.1** |
| CORN OIL | 72 | 8.5 | 8.8 | 0.3 N.S. |

** $p < 0.02$

As appears from the table the activity is reduced significantly with the composition according to the present application, whereas no significant effect is reached with corn oil.

According to the the results shown in the tables 3–11 above, a composition according to present application has a significant effect on all the above mentioned risk factors for cardiovascular diseases. In comparison some positive results are obtained with corn oil but no significant effect is obtained for blood pressure, the level of serum triglycerides or for the activity of the coagulation factor VII. Further the effects measured in the corn oil group for these risk factors seem to be going in the opposite direction, being detrimental.

Thus fatty acid compositions according to the present invention are potentially valuable for the treatment and prophylaxis of multiple risk factors known for cardiovascular diseases, such as hypertension, hypertriglyceridemia and high coagulation factor VII phospholipid complex activity.

The doses of the composition of this invention needed for therapeutic or prophylatic effect will vary with the type of administration. In our large scale tests we administered 6 grams per person per day of the test composition. Generally for the average adult person the doses may vary from 1.0 to 10 grams depending upon body size and the seriousness of the condition to be treated.

The compositions according to the present application may further be used as an additional drug to the customary hypertensive drug in treatment of hypertension. The doses will presumably lie in the lower part of the above mentioned dosage range.

Other possible medical indications for which the compositions according to the present application may be administered are chronic polyarthritis, psoriatic artheritis, periarteritis nodosa, lupus erythematosus disseminatus (LED), sclerodermia, Crohn's disease, ulcerative colitis, psoriasis, atopic dermatitis and migraine as has been indicated in standard in vivo tests.

Perferably the active compounds should be orally administered in the form of pills, soft capsules or the like. However, the administration could also be through any other route where the active ingredients may be efficiently absorbed and utilized, e.g. intravenously, subcutaneously, rectally, vaginally or possibly topically.

The pharmaceutical composition may eventually comprise, in addition to the EPA and DHA active ingredients as defined, one or more pharmaceutically acceptable carriers as well known in the art. The compositions can also include fillers, stabilizers, extenders, binders, humidifiers, surfactants, lubricants and the like, as known in the art of formulating pharmaceutical composition.

In addition antioxidants, for example hydroxytoluene, butyrate, quinone, tocopherol, ascorbic acid etc., preservatives, colouring agents, perfumes, flavourings and other pharmaceutical agents may be used.

EXAMPLE OF PHARMACEUTICAL PREPARATION

| Soft gelatine capsules containing 1 g/per capsule Composition: | |
| --- | --- |
| EPA ethyl ester | 525 mg/capsule |
| DHA ethyl ester | 315 mg/capsule |
| d-alpha Tocopherol | 4 mg/capsule |
| Gelatine | 246 mg/capsule |
| Glycerol | 118 mg/capsule |
| Red iron oxide | 2.27 mg/capsule |
| Yellow iron oxide | 2.27 mg/capsule |

The active ingredients and the excipients are weighed and homogenized on a high speed stirrer. The mixture is then colloid milled and deareated in a stainless steel vessel ready for encapsulation. The mixture is filled in soft gelatine capsules of size 20 oblong (average weight 1.4 g) using a standard capsulation machine.

We claim:

1. A method for the treatment or prophylaxis of hypertriglyceridemia in a human patient, which comprises orally administering to the patient a pharmaceutical composition in which the active ingredients consist essentially of a mixture of fatty acids of which at least 80% by weight is comprised of a combination of (all-Z omega-3)-5,8,11,14,17-eicosapentaenoic acid (EPA) and (all-Z omega-3)-4,7,10,13,16,19-docosahexaenoic acid (DHA) in a weight ratio of EPA:DHA of from 1:2 to 2:1, said composition being administered in amounts providing a daily dosage of 1 to 10 grams of said mixture of fatty acids.

2. The method of claim 1, wherein at least 85% by weight of the mixture of fatty acids is comprised of long chain omega-3 fatty acids.

3. The method of claim 2, wherein the EPA constitutes 40 to 60% by weight of the mixture of fatty acids and the DHA constitutes 25 to 45% by weight of the mixture of fatty acids.

4. The method of claim 3, wherein the EPA and DHA are present in the composition in an EPA:DHA weight ratio of from 1:1 to 2:1.

5. The method of claim 4, wherein at least 4.5% by weight of the mixture of fatty acids is comprised of fatty acids other than EPA and DHA that have 20, 21, or 22 carbon atoms.

6. The method of claim 4, wherein at least 3% by weight of the mixture of fatty acids is comprised of omega-3 fatty acids other than EPA and DHA that have 20, 21, or 22 carbon atoms.

7. The method of claim 4, wherein at least 1% by weight of the mixture of fatty acids is comprised of (all-Z omega-3)-6,9,12,15,18-heneicosapentaenoic acid.

8. The method of any of claims 5, 6, or 7, wherein the fatty acids are present in the composition in esterified form.

9. The method of any of claims 5, 6, or 7, wherein the fatty acids are present in the composition in ethyl ester form.

10. The method of any of claims 5, 6, or 7, wherein the fatty acids are present in the composition in salt form.

11. The method of any of claims 5, 6, or 7, wherein the fatty acids are present in the composition in the free acid form.

12. The method of claim 7, wherein at least 85% by weight of the fatty acid content of the composition is comprised of the combination of EPA and DHA, and the fatty acids are present in the composition in ethyl ester form.

* * * * *

UNITED STATES PATENT AND TRADEMARK OFFICE
CERTIFICATE OF CORRECTION

PATENT NO. : 5,502,077

DATED : March 26, 1996

INVENTOR(S) : Breivik et al.

It is certified that error appears in the above-indentified patent and that said Letters Patent is hereby corrected as shown below:

On the title page, under item [56]

FOREIGN PATENT DOCUMENTS:

"WO88008444 11/1988 WIPO" should read --WO88/08444 11/1988 WIPO--.
Please insert: --2218984 11/1989 Great Britain--.

OTHER PUBLICATIONS:

After "Kinsella et al." insert --,-- (a comma), and change "pp. 7+08" to --pp 7-8--.
Please insert: --Harrison's Principles of Internal Medicine, 11th ed. (Braunwald et al., eds), McGraw-Hill, New York, p. 1204--.

Primary Examiner:

Mukund J.g232 2 Shah" should read --Mukund J. Shah--.

COLUMN 4,

Line 12, "analyzis" should read --analysis--.

COLUMN 5,

In Table 1, line 3, "1,4" should read --1.4--;
line 7, "32,6" should read --32.6--; and
line 8, "3-8,5" should read --3-8.5-;
and "7,5" should read --7.5--.

UNITED STATES PATENT AND TRADEMARK OFFICE
CERTIFICATE OF CORRECTION

PATENT NO. : 5,502,077
DATED : March 26, 1996
INVENTOR(S) : Breivik et al.

It is certified that error appears in the above-indentified patent and that said Letters Patent is hereby corrected as shown below:

COLUMN 6:

In Table 3, last line, "EPA:DRA" should read --EPA:DHA--.

COLUMN 7,

At Table 5, line 8, "(mm HG)" should read --(mm Hg)--, and "(mg Hg)" should read --(mm Hg)--.

COLUMN 9,

At Table 10, line 6, "X SEM" should read --$\bar{X}$ SEM--.

COLUMN 11,

Line 34, "4 mg/capsule" should read --4 IU/capsule--.

Signed and Sealed this

Twentieth Day of August, 1996

Attest:

BRUCE LEHMAN

*Attesting Officer*   *Commissioner of Patents and Trademarks*